US005626615A

United States Patent [19]

Keller et al.

[11] Patent Number: 5,626,615

[45] Date of Patent: May 6, 1997

[54] CHIROPRACTIC ADJUSTING INSTRUMENT

[75] Inventors: Tony S. Keller, Burlington, Vt.; Arlan W. Fuhr, Phoenix, Ariz.

[73] Assignee: Activator Methods, Inc., Phoenix, Ariz.

[21] Appl. No.: 515,521

[22] Filed: Aug. 15, 1995

Related U.S. Application Data

[63] Continuation-in-part of Ser. No. 39,207, May 23, 1995, Pat. No. Des. 374,081, which is a continuation-in-part of Ser. No. 489,102, Jun. 9, 1995.

[51] Int. Cl.$^{6}$ .................................................. A61F 5/00

[52] U.S. Cl. ...................... 606/238; 606/237; 606/239; 601/107; 601/108

[58] Field of Search .............................. 601/108, 107, 601/109, 110, 111; 606/237, 238, 239, 240, 241

[56] References Cited

U.S. PATENT DOCUMENTS

| | | | |
|---|---|---|---|
| 2,421,354 | 5/1947 | Reiter | 128/305 |
| 4,116,235 | 9/1978 | Fuhr et al. | |
| 4,461,286 | 7/1984 | Sweat | 606/238 |
| 4,498,464 | 2/1985 | Morgan, Jr. | 128/54 |
| 4,669,454 | 6/1987 | Shamos | 606/238 |
| 4,682,490 | 7/1987 | Adelman et al. | 73/12 |
| 4,841,955 | 6/1989 | Evans et al. | 128/52 |
| 4,984,127 | 1/1991 | Evans et al. | 361/179 |
| 5,103,806 | 4/1992 | McLeod et al. | 128/24 AA |

OTHER PUBLICATIONS

Advertising Brochure by Activator Methods, Inc. for "Activator Instrument" and Instrument/Cervical Tip (dated Jan./Feb., 1994; pp. 1 and 10.

Journal Article by Osterbauer, De Boer, Widmaier, Petermann & Fuhr entitled "Treatment and Biomechanical Assessment of Patients with Chronic Sacroiliac Joint Syndrome" (published in the Feb. 1993 edition of Journal of Manipulative and Physiological Therapeutics.)

*Primary Examiner*—Michael Buiz
*Assistant Examiner*—Mark S. Leonardo
*Attorney, Agent, or Firm*—Leydig, Voit & Mayer, Ltd.

[57] ABSTRACT

An improved chiropractic adjusting instrument is provided for use in spinal manipulative therapy and for exciting a human spine at its natural frequency. The chiropractic adjusting instrument includes a thrust element for delivering an input force, a body contact member removably attached to the thrust element, a spring means for propelling the thrust element and the body contact member outwardly, and an adjustment knob arranged on the thrust element for adjusting the amount of potential energy imposed on the spring means and for controlling the magnitude of the resulting input force. In use, the input force is mechanically tuned to a desired frequency (e.g., the natural frequency of a human spine) by positioning a shaped mass on the thrust element. By mechanically tuning the chiropractic adjusting instrument in this way, the dynamic output response of the spine is maximized while the requisite impact force is minimized. This not only enhances the overall effectiveness of spinal manipulative therapy, but also reduces the possibility of damage to the vertebrae during such treatment.

6 Claims, 2 Drawing Sheets

CHIROPRACTIC ADJUSTING INSTRUMENT

This application is a continuation-in-part of U.S. application Ser. No. 29/039,207, filed on May 23, 1995, now U.S. Pat. No. 5,374,081 and which is a continuation-in-part of U.S. application Ser. No. 08/489,102, filed on Jun. 9, 1995.

BACKGROUND OF THE INVENTION

1. Field of the Invention

The present invention relates generally to the chiropractic adjustment of musculoskeletal structures, and more particularly concerns an improved chiropractic adjusting instrument for use in spinal manipulative therapy.

2. Description of the Prior Art

The chiropractic art is generally concerned with adjusting misaligned body structures by manually manipulating the various joints in the human body. Of more specific interest in the art, however, is the spinal column which is comprised of several interconnected musculoskeletal structures or vertebrae. Unlike other, less critical body structures, the spinal column must be treated or manipulated with extreme caution because of its link with the central nervous system.

The human spine is susceptible to many different pathologic abnormalities including misalignment, miscellaneous trauma and pain, and degeneration as a result of age or disease. By employing various physical therapy techniques, though, a chiropractor, or one skilled in the chiropractic art, may be able to successfully treat a pathologic spine. Successful treatment will not only relieve any pain or discomfort that the patient might be suffering, but will also improve the overall quality of life of that patient.

One common spinal-adjustment technique involves applying thrusts or forces to the afflicted region of the spine. In particular, this technique involves either "mobilizing" the spine (i.e. passively moving the spine with relatively slow cyclic or oscillatory motion), or "manipulating" the spine (i.e. applying an impulsive thrust or force in a well-defined direction to a specific region of the spine). Depending on professional affiliations, this technique is referred to as chiropractic adjustment, osteopathic manipulation, orthopaedic manual therapy, and/or spinal manipulative therapy.

There are several well known procedures or techniques for "manipulating" or administering impulsive thrusts to a spine. One technique involves applying one or more rapid thumb thrusts to misaligned or afflicted vertebrae. Thumb thrusts, however, tend to be both imprecise in magnitude and location and tiresome to administer. Another technique involves using a manually operated chiropractic adjusting instrument. For instance, U.S. Pat. No. 4,116,235, issued to Fuhr et al. ("Fuhr") and U.S. Pat. No. 4,498,464, issued to Morgan, Jr., disclose such instruments.

The Fuhr device, in particular, is a manually operated, spring-loaded device for delivering an impact force or thrust to a patient's spine at a rapid speed and in a precise line of drive. Further, although the magnitude of the impact force delivered by the Fuhr device is adjustable, the frequency at which the impact force is delivered is completely arbitrary. As such, the Fuhr device is not mechanically "tuned" to any particular frequency.

The ability to "tune" a chiropractic adjusting instrument to a desired frequency, though, would offer the chiropractic clinician several significant advantages over the prior art. For instance, a chiropractic adjusting instrument that is "tuned" or "tunable" to the natural frequency of a human spine would maximize the dynamic motion response of the spine while, at the same time, minimize the magnitude of the requisite impact force. Such a chiropractic adjusting instrument would not only enhance the overall effectiveness of spinal manipulative therapy, but would also decrease the possibility of damage to the vertebrae during such treatment.

OBJECTS AND SUMMARY OF THE INVENTION

The primary object of the present invention is to provide an improved chiropractic adjusting instrument which is "tunable" to a desired frequency.

A more specific object of the present invention is to provide an improved chiropractic adjusting instrument which is "tunable" to the natural frequency of a musculoskeletal structure.

An even more specific object of the present invention is to provide an improved chiropractic adjusting instrument which is "tunable" to the natural frequency of a human spine.

Another object of the present invention is to provide an improved chiropractic adjusting instrument of the foregoing type which is reliable, precise, and convenient to use.

A further object of the present invention is to provide a method of adjusting a spinal column by exciting the spinal column at its natural frequency.

These and other features and advantages of the invention will become apparent upon reading the following description of a preferred exemplified embodiment of the invention, and upon reference to the accompanying drawings wherein:

While the invention will be described and disclosed in connection with certain preferred embodiments and procedures, it is not intended to limit the invention to those specific embodiments. Rather it is intended to cover all such alternative embodiments and modifications as fall within the spirit and scope of the appended claims.

DETAILED DESCRIPTION OF THE PREFERRED EMBODIMENT

Figure 1:
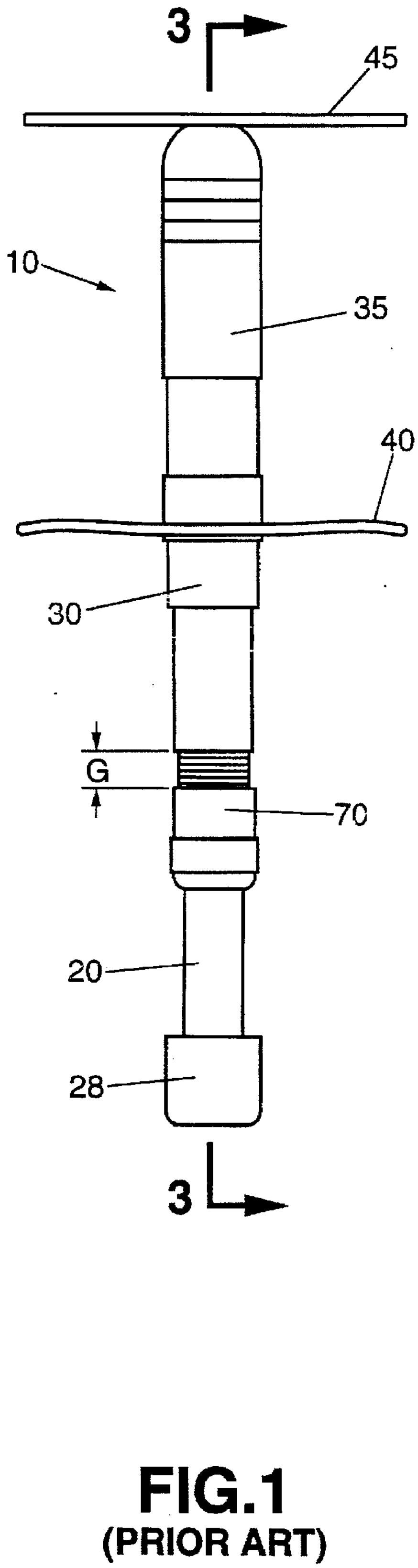
FIG.1 (PRIOR ART)
FIG. 1 is a side view of a prior art chiropractic adjusting instrument.
Figure 3:
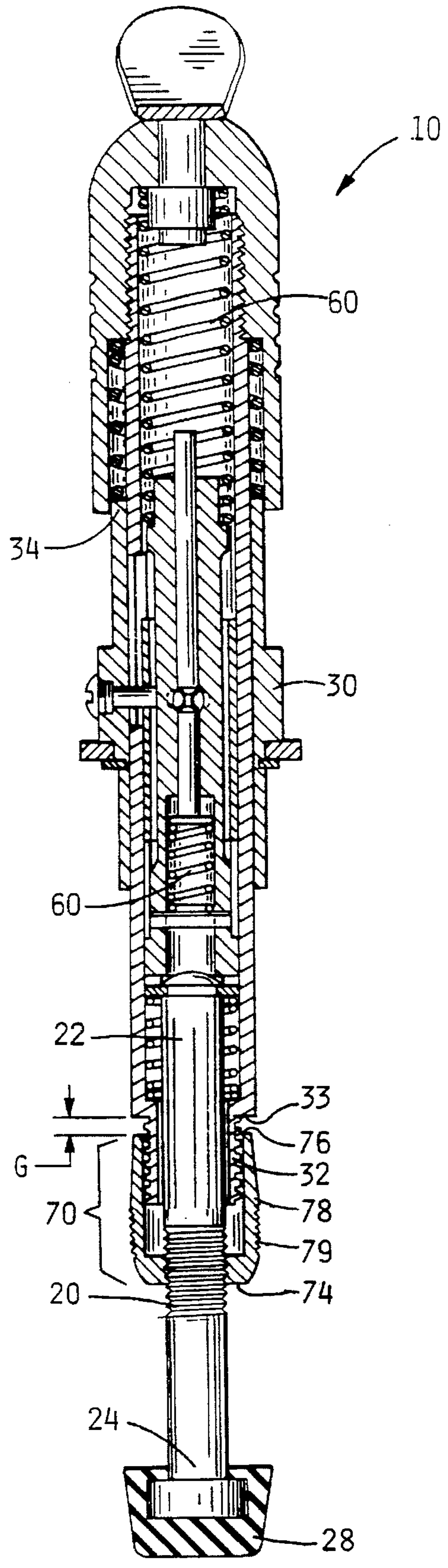
FIG. 3 (PRIOR ART)
FIG. 3 is a cross-sectional view of the prior art chiropractic adjusting instrument taken along line 3—3 in FIG. 1.

Referring now specifically to the drawings, FIGS. 1 and 3 depict the prior art chiropractic adjusting instrument 10 disclosed in the Fuhr patent (i.e. the Fuhr device). In particular, the Fuhr device is a manually operated chiropractic posterior-anterior adjusting instrument 10 which broadly comprises: a thrust element 20; a removable body contact member 28; a main body 30; an end cap 35; a first handle member 40; a second handle member 45; a spring means 60 for propelling the thrust element 20 outwardly; and a trigger means for actuating the spring means 60.

The thrust element 20 of the prior art chiropractic adjusting instrument 10 comprises a shank portion 22 and an outer end portion 24. As shown in FIG. 3, the removable body contact member 28 is positioned adjacent to the outer end portion 24 of the thrust element 20. Preferably, the removable body contact member 28, made of a resilient material such as rubber, soft plastic, or the like.

The main body 30 has a first end 32, which longitudinally slidably receives the shank portion 22 of the thrust element 20, and a second end 34. The end cap 35 is swivelly and longitudinally slidably mounted on the second end 34 of the main body 30.

As best depicted in FIG. 1, the first and second handle members 40, 45 are arranged in spaced relation to one another. In particular, the first handle member 40 is rotatably disposed on the main body 30, the second handle member 45 is fixedly disposed on the end cap 35, and the first and second handle members 40, 45 are squeezably disposed relative to one another. In operation, as the first and second handle members 40, 45 are squeezed together, the shank portion 22 of the thrust element 20 retracts inwardly within the main body 30 which compresses the spring means 60. Ultimately, when the first and second handle members 40, 45 have been squeezed together a predetermined distance, the trigger means releases or actuates the spring means 60 and the thrust element 20 is propelled rapidly outwardly. For a complete disclosure of the structure and operation of the trigger means, see column 3, line 51 through column 4, line 62 of the Fuhr patent.

The Fuhr device 10 also comprises a calibration means for controlling the amount that the shank portion 22 of the thrust element 20 retracts within the main body 30 when the first and second handle portions 40, 45 are squeezed together, for controlling the amount of potential energy imposed on the spring means 60, and, more particularly, for adjusting the amplitude of the input force delivered to the musculoskeletal structure. In the illustrated embodiment, the calibration means comprises an adjustment knob 70 having an internally threaded end 74, a non-threaded end 76, and a sleeve portion disposed therebetween 78. As shown in FIG. 3, the internally threaded end 74 of the adjustment knob 70 is screwably disposed the thrust element 20 such that a gap G, or initial spacing, exists between the non-threaded end 76 and the flange 33 of the main body 30. In use, when the first and second handle members 40, 45 are squeezed together, the non-threaded end 76 engages the flange 33. As such, the gap G not only predefines the amount that the shank portion 22 of the thrust element 20 can retract within the main body 30, but also controls the amount of potential energy imposed on the spring means 60 as well as the magnitude of the input force that is delivered by the adjusting instrument 10 (i.e. a larger gap G denotes a higher amplitude input force). Calibration of the chiropractic adjustment instrument 10 is thus accomplished simply by turning or screwing the adjustment knob 70 to the desired position. In the illustrated embodiment of the Fuhr device, the sleeve portion 78 of the adjustment knob 70 is also provided with a knurled portion 79 which facilitates the turning and positioning of the adjustment knob 70.

In accordance with certain objects of the present invention, the Fuhr device has been improved such that the input force delivered by the chiropractic adjusting instrument 10 is now "tuned" or is "tunable" to the natural frequency of the musculoskeletal structure being examined. These objects are achieved either: (1) by varying the mass and/or shape of the thrust element 20; (2) by modifying the stiffness of the removable body contact member 28; or (3) by altering the stiffness of the spring means 60.

Figure 2:
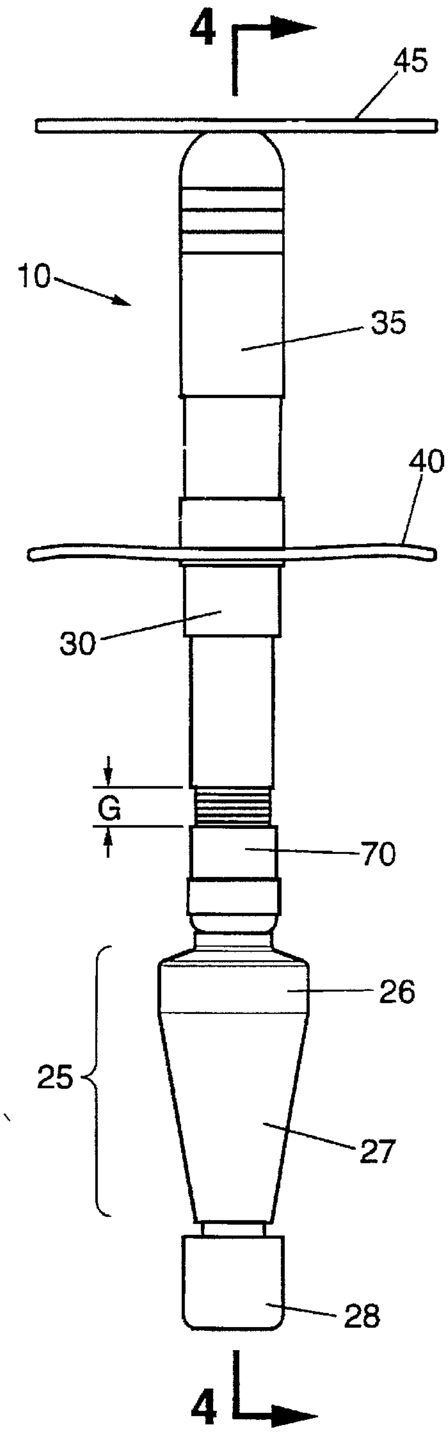
FIG. 2 is a side view of an improved chiropractic adjusting instrument having a shaped mass which mechanically tunes the instrument to a desired frequency.
Figure 4:
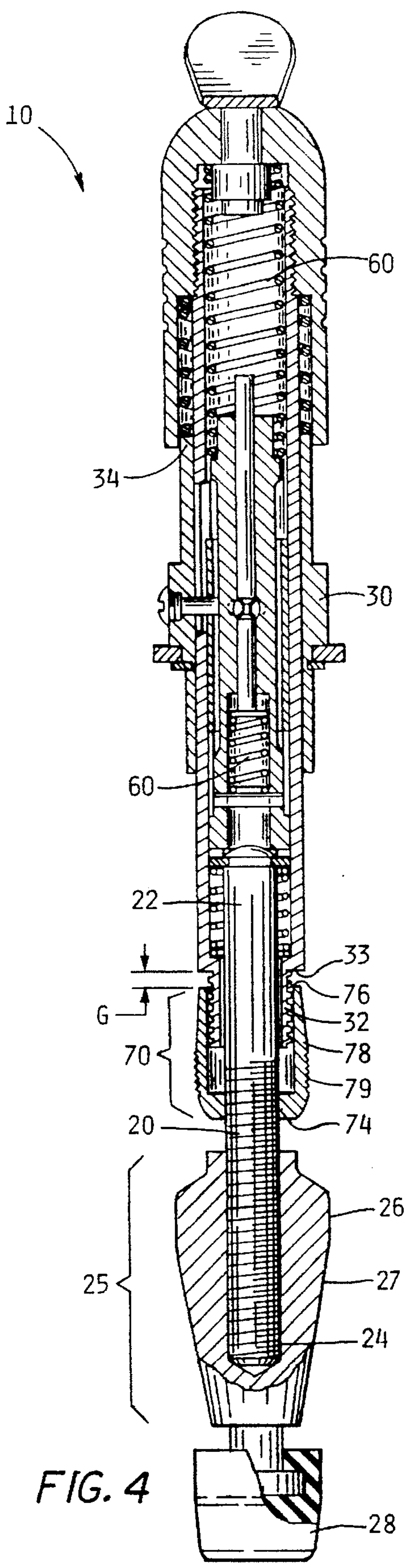
FIG. 4 is a cross-sectional view of the improved chiropractic adjusting instrument taken along line 4—4 in FIG. 2.

A first embodiment of a mechanically tuned chiropractic adjusting instrument 10 is illustrated in FIGS. 2 and 4. In particular, the first embodiment generally comprises a shaped mass 25 positioned on the thrust element 20 and disposed generally between the main body 30 and the removable body contact member 28. In the illustrated embodiment, the shaped mass 25 screwably receives the outer end portion 24 of the thrust element 20, as shown in FIG. 4. It will be readily apparent to those skilled in the art, however, that the shaped mass 25 could be positioned on the thrust element 20 in other ways.

As shown in FIGS. 2 and 4, the shaped mass 25 has a generally cylindrical portion 26 and a generally conical portion 27 which tapers inwardly from the generally cylindrical portion 26. Moreover, the shaped mass 25 is arranged on the thrust element 20 such that the generally cylindrical portion 26 faces the first handle member 40 while the generally conical portion 27 faces the removable body contact member 28. It will be appreciated, however, that both the configuration and the orientation of the shaped mass 25 could be modified from the specific embodiment disclosed herein.

In keeping with an important aspect of the present invention, the first embodiment of the chiropractic adjusting instrument 10 is mechanically tuned to the natural frequency of most human spinal columns. More importantly, though, the frequency at which the chiropractic adjustment instrument 10 is mechanically tuned to can be adjusted—between a range of about 1 hertz to about 60 hertz—simply by changing the mass, size, shape, and/or arrangement of the shaped mass 25.

In addition, once the chiropractic adjusting instrument 10 is "tuned" to the natural frequency of a particular spine, that spine can then be excited at its natural frequency. Thus, in spinal manipulative therapy, the dynamic output response of the spine is maximized while the magnitude of the impact force delivered to the spine is minimized. This not only increases the overall effectiveness of spinal manipulative therapy but also significantly reduces the risk of vertebrae damage.

A second embodiment of a mechanically tuned chiropractic adjusting instrument 10 (not shown) involves modifying the relative stiffness of the removable body contact member in order to mechanically tune the chiropractic adjusting instrument 10 to the natural frequency of the musculoskeletal structure (or spine) of interest. The inventors have discovered that by varying relative stiffness of the removable contact member 28 between about 30 and 80 durometer, the mechanical tuning of the chiropractic adjusting instrument 10 can be appreciable altered without sacrificing patient comfort.

A third embodiment of a mechanically tuned chiropractic adjusting instrument 10 (not shown) involves altering the relative stiffness of the spring means 60. By changing the relative stiffness of the spring means 60, the mechanical tuning of the chiropractic adjusting instrument 10 can also be noticeably altered.

We claim as our invention:

1. An improved chiropractic adjusting instrument of the type having:

- a thrust element including a shank portion and an outer end portion;
- a removable body contact member positioned adjacent to the outer end portion of the thrust element;
- a main body having a first end and a second end, the first end longitudinally slidably receiving the shank portion of the thrust element;
- an end cap longitudinally slidably mounted on the second end of the main body;

a first handle member disposed on the main body;

a second handle member disposed on the end cap;

the first handle member being squeezably disposed relative to the second handle member such that the first handle member moves toward the second handle member and the shank portion of the thrust element retracts inwardly within the main body when the first and second handle members are squeezed together;

an adjustment knob movably disposed on the thrust element for controlling retraction of the shank portion of the thrust element within the main body when the first and second handle members are squeezed together;

a spring means disposed within the main body for propelling the thrust element outwardly; and a trigger means for actuating the spring means when the first and second handle members have been squeezed together a predetermined distance, wherein the improvement comprises:

a shaped mass positioned on the thrust element and disposed between the removable body contact member and the adjustment knob for mechanically tuning the chiropractic adjusting instrument to a desired frequency.

2. An apparatus as set forth in claim 1 wherein the shaped mass includes a generally cylindrical portion and a generally conical portion.

3. An apparatus as set forth in claim 2 wherein the generally cylindrical portion of the shaped mass is arranged facing the first handle member and the generally conical portion of the shaped mass is arranged facing the removable body contact member.

4. An apparatus as set forth in claim 1 wherein the shaped mass mechanically tunes the chiropractic adjusting instrument to a frequency ranging between about 1 hertz and about 60 hertz.

5. An apparatus as set forth in claim 1 wherein the desired frequency is the natural frequency of a musculoskeletal structure.

6. An apparatus as set forth in claim 5 wherein the musculoskeletal structure is a human spine.

* * * * *